(12) United States Patent
Persad et al.

(10) Patent No.: US 6,647,581 B1
(45) Date of Patent: Nov. 18, 2003

(54) TONGUE CLEANER INSIDE TOOTHBRUSH HANDLE

(76) Inventors: Vaughn Persad, 1310 Carlsbad Pl., Orlando, FL (US) 32808; Monica Persad, 1310 Carlsbad Pl., Orlando, FL (US) 32808

( * ) Notice: Subject to any disclaimer, the term of this patent is extended or adjusted under 35 U.S.C. 154(b) by 0 days.

(21) Appl. No.: 10/092,626

(22) Filed: Jun. 27, 2002

(51) Int. Cl.[7] ............................ A46B 15/00; A61B 17/24
(52) U.S. Cl. ........................ 15/111; 132/309; 606/161
(58) Field of Search ........................ 15/111, 167.1; 132/309; 606/161

(56) References Cited

U.S. PATENT DOCUMENTS

| | | | | |
|---|---|---|---|---|
| 1,893,524 A | * | 1/1933 | Shanley | 606/161 |
| 5,005,246 A | * | 4/1991 | Yen-Hui | 15/111 |
| 5,881,422 A | * | 3/1999 | Narwani | 15/111 |

FOREIGN PATENT DOCUMENTS

| | | | | |
|---|---|---|---|---|
| FR | 734846 | * | 10/1932 | 606/161 |
| GB | 13341 | * | of 1894 | 132/309 |
| GB | 2027347 | * | 2/1980 | |
| GB | 2252909 | * | 8/1992 | |

* cited by examiner

*Primary Examiner*—Mark Spisich

(57) ABSTRACT

A tongue cleaner being fitted into a hollow opening inside the handle of a toothbrush. It is very accessible from the handle like a pocket knife. The material of the tongue cleaner is made of plastic, 0.5 mm in thickness, about 12 cm long, and 1 cm in width. The material can be easily bent in a v-shape pattern because in the center of the tongue cleaner there is a slight depression of 1 mm in the width of the material.

1 Claim, 2 Drawing Sheets

TONGUE CLEANER INSIDE TOOTHBRUSH HANDLE

BACKGROUND OF INVENTION

1. Field of the Invention

This invention relates to a replaceable toothbrush which contains a tongue cleaner positioned in an elongated hallowed section inside toothbrush handle, which serves in providing complete oral care, including cleaning of the teeth and the tongue.

2. Description of the Prior Art

For years, dentists have recommended that you brush at least twice a day and floss once a day to maintain healthy teeth and gums, and to prevent bad breath. However, many oral care experts do not mention that up to eighty-five percent of odor causing bacteria are found on the surface of the tongue, as recent studies have shown. Some dentists recommend that their patients simply brush their tongue, as they do their teeth. However, this practice is very harsh and aggressive to the tongue, and can be very discomfortable and unproductive.

Other inventions have attempted to solve this problem, however most have been very unsuccessful due to an array of reasons:

1. Other tongue scrapers are not flexible, and are manufactured to fit the "standard" tongue, thus not taking into account that every individual differs.
2. The shapes of prior tongue cleaners prevent them from reaching the farthest back of the tongue; therefore cleaning is kept at a minimum.
3. Some preceding tongue cleaners, due to their irregular shape, can cause the user to experience a gagging-reflex and an abrasive feeling on the tongue's surface. In addition, because of the shapes, they are very challenging to clean.
4. Most tongue cleaners are expensive and difficult to manufacture, thus they are very uneconomical.

SUMMARY OF THE INVENTION

The key object of this invention is to combine a standard toothbrush and tongue cleaner in one, in order to provide easy and convenient access to both necessary oral care products at the same time.

Another object of this invention is to provide a flexible plastic tongue cleaner that can easily be adjusted to best fit the mouth of every individual, with the least discomfort to the user.

Another object of this invention is to provide the most thorough cleaning of the tongue's surface by: (1) reaching farthest back on the tongue, which is allowed by the V-shape of the tome cleaner, and (2) by covering the entire tongue's surface area, which is allowed by the flexibility of the tongue cleaner.

Another object of this invention is to allow for non-abrasive cleaning of the tongue and to reduce the gagging-reflex.

Another object of this invention is to allow for easy accessibility of tongue cleaner through the finger grip, and to allow for easy and thorough cleaning of both tongue cleaner and toothbrush.

It is yet another object of this invention to provide easy and inexpensive manufacturing.

DETAILED DESCRIPTION OF THE PREFERRED EMBODIMENT

Figure 1:
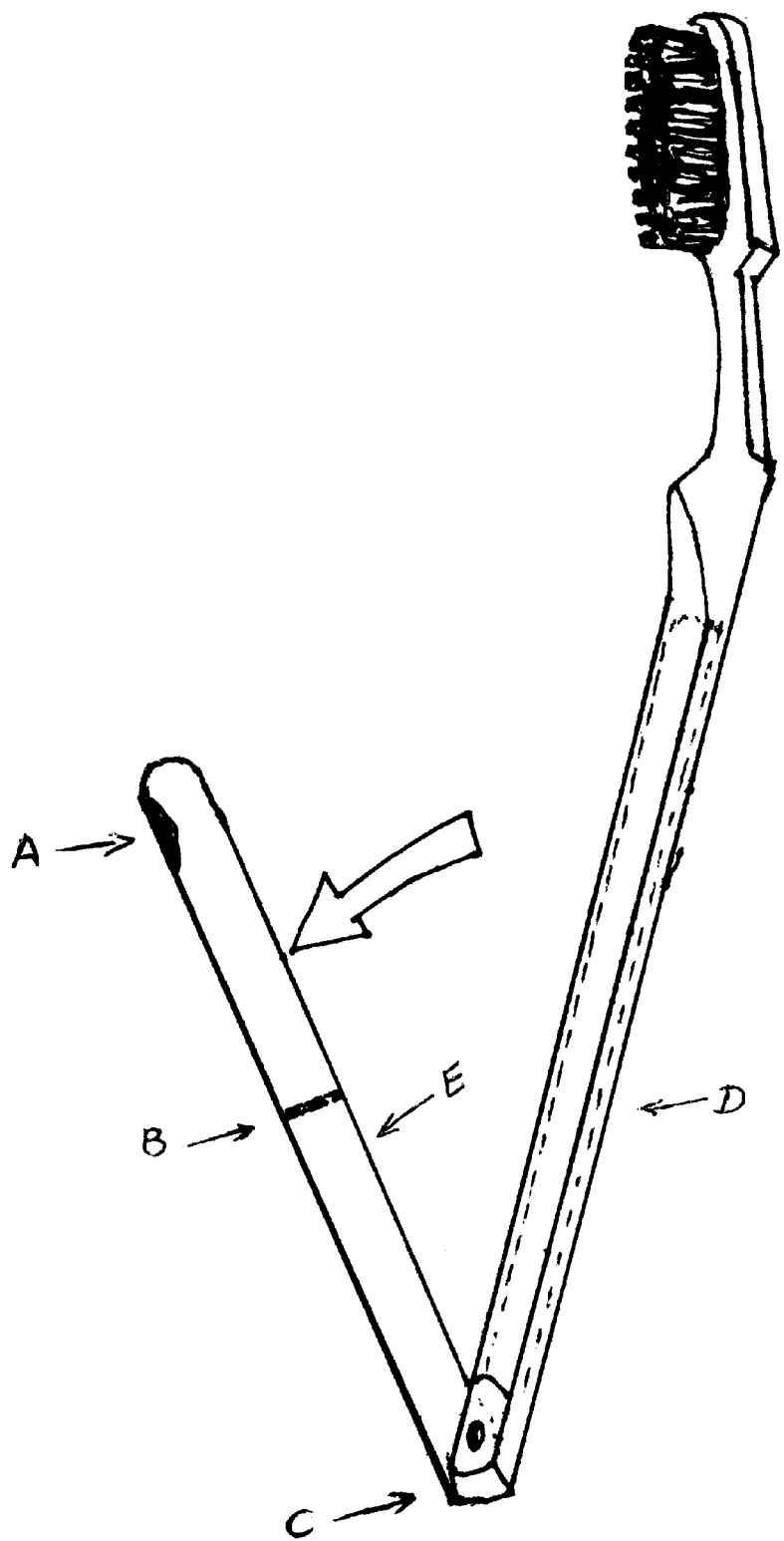
FIG. 1 shows a side view of the toothbrush and tongue cleaner in one, wherein the tongue cleaner is pivotally attached to the bottom end of the toothbrush handle.

Reference will now be made to FIG. 1, in which A is finger grip indentation, B is a slight depression in center to tongue scraper, C is where the tongue scraper is pivotally attached to the toothbrush handle, D is the elongated hollowed section in which the tongue cleaner is stored, and E is the tongue cleaner as a whole.

The tongue cleaner E can be manufactured using a plastic such as polyethylene. It is approximately 12 centimeters in length, 1 cm in width, and 0.5 millimeter in thickness. The length, width, and thickness can be varied due to manufacturer or user preference. This tongue cleaning device is pivotally connected at C.

Figure 2:
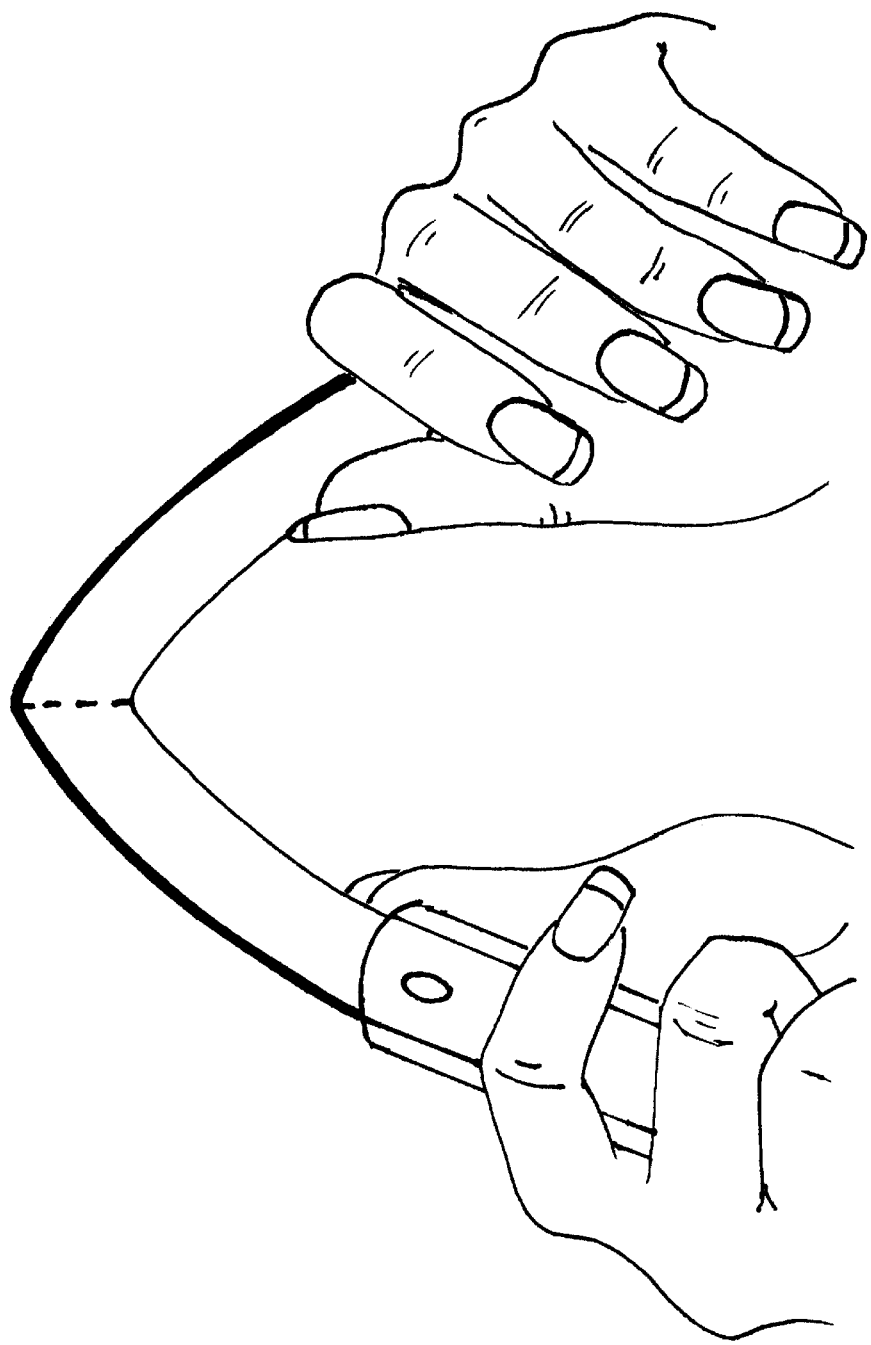
FIG. 2 illustrates how the tongue cleaner can be bent into a V-shape for usage.

The tongue cleaner E has a finger-grip pattern A, which allows for easy opening of the tongue cleaner when stored inside of the toothbrush handle D. In the middle of the tongue cleaner E, there is a slight depression B thats allows the tongue cleaner to bend into a V-shape, as shown in FIG. 2. This depression is approximately 1 millimeter in width.

The tongue cleaner E is intended to be retrieved from inside the handle after brushing, and extended to be in line with the toothbrush handle. The user will then hold the toothbrush handle near C with one hand and hold near A with the other hand. Next, the user will slightly bend the tongue cleaner into a V-shape that will easily fit into the mouth. This positioning is illustrated in FIG. 2. The user will then extend his/her tongue from the mouth, then position the tongue cleaner on the far back of the tongue. Gently pressing downward, the user will pull forward with a stroking motion out to the tip of the tongue. This procedure can be repeated until tongue is thoroughly cleaned. Once debris has collected on the surface of the tongue cleaner, it can be rinsed with water to be cleaned.

What is claimed is:

1. An oral care device comprising:

a toothbrush comprising an elongated handle having a brush head at a first end thereof, said handle further including an elongate hollowed section extending from an opposite second end of the handle towards the brush head; and an elongated plastic tongue cleaner including first and second ends, the second end of the tongue cleaner is pivotally connected to the second end of the handle whereby the tongue cleaner may be retracted within the hollowed section to the handle when not in use and retracted therefrom during use, the first end of the tongue cleaner including a finger grip pattern adjacent thereto for facilitating the retrieval of the tongue cleaner from within the handle, a center portion of the tongue cleaner including a narrow slight depression extending across a width thereof whereby the tongue cleaner may be bent about said depression.

* * * * *